US009044241B2

(12) United States Patent
Barner et al.

(10) Patent No.: US 9,044,241 B2
(45) Date of Patent: Jun. 2, 2015

(54) BUSHING ARM DEFORMATION MECHANISM

(71) Applicant: BOSTON SCIENTIFIC SCIMED, INC., Maple Grove, MN (US)

(72) Inventors: Paul Barner, Newton, MA (US); Laura Firstenberg, Worcester, MA (US); Craig McGreevy, South Berwick, ME (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 153 days.

(21) Appl. No.: 13/889,547

(22) Filed: May 8, 2013

(65) Prior Publication Data

US 2013/0304095 A1 Nov. 14, 2013

Related U.S. Application Data

(60) Provisional application No. 61/644,780, filed on May 9, 2012.

(51) Int. Cl.

| A61B 17/10 | (2006.01) |
|---|---|
| A61B 17/128 | (2006.01) |
| B66C 1/42 | (2006.01) |
| A61B 17/122 | (2006.01) |
| A61B 17/00 | (2006.01) |
| A61B 19/00 | (2006.01) |
| A61B 17/064 | (2006.01) |

(52) U.S. Cl.
CPC .............. *A61B 17/1285* (2013.01); *B66C 1/42* (2013.01); *A61B 17/122* (2013.01); *A61B 17/1227* (2013.01); *A61B 2017/00951* (2013.01); *A61B 2019/304* (2013.01); *A61B 2019/307* (2013.01); *A61B 17/0643* (2013.01)

(58) Field of Classification Search
CPC ............. A61B 17/122; A61B 17/1227; A61B 17/1285; A61B 2019/307
USPC .................. 606/143, 142, 151, 157, 139, 195, 606/205–209, 120, 158
See application file for complete search history.

(56) References Cited

U.S. PATENT DOCUMENTS

| 8,152,822 B2 * | 4/2012 | Gayzik .......................... 606/151 |
|---|---|---|
| 2008/0306491 A1 * | 12/2008 | Cohen et al. ................... 606/142 |

(Continued)

FOREIGN PATENT DOCUMENTS

WO      2008/127525      10/2008

*Primary Examiner* — Todd Manahan
*Assistant Examiner* — Majid Jamialahmadi
(74) *Attorney, Agent, or Firm* — Fay Kaplun & Marcin, LLP

(57) ABSTRACT

A medical device includes (a) a capsule including a lumen extending therethrough, a proximal end of the capsule including at least one window extending therethrough; (b) a bushing including a channel extending therethrough, a distal end including at least one arm extending distally therefrom such that a corresponding one of the arms is releasably engagable with a corresponding one of the windows; and (c) a core member including a locking portion and at least one engaging element. The locking portion is sized and shaped to be received within the channel of the bushing to apply a pressure to the arm such that the arm engages the windows. The engaging element extends laterally outward from a portion of the core member such that the engaging element engages a corresponding one of the arms to deform the arms radially inward and out of engagement with the windows.

9 Claims, 3 Drawing Sheets

(56) References Cited

U.S. PATENT DOCUMENTS

| | | |
|---|---|---|
| 2009/0163934 A1 | 6/2009 | Raschdorf, Jr. et al. |
| 2010/0152753 A1* | 6/2010 | Menn et al. ............ 606/158 |
| 2011/0046651 A1* | 2/2011 | Cohen et al. ............ 606/157 |
| 2012/0065646 A1* | 3/2012 | Phillips-Hungerford et al. ............ 606/142 |
| 2013/0226199 A1* | 8/2013 | Harris et al. ............ 606/142 |

* cited by examiner

BUSHING ARM DEFORMATION MECHANISM

PRIORITY CLAIM

This application claims the priority to the U.S. Provisional Application Ser. No. 61/644,780, entitled "BUSHING ARM DEFORMATION MECHANISM" filed on May 9, 2012. The specification of the above-identified application is incorporated herewith by reference.

BACKGROUND

Pathologies of the gastrointestinal ("GI") system, the biliary tree, the vascular system and other body lumens and hollow organs are often treated through endoscopic procedures, many of which require active and/or prophylactic hemostasis to control bleeding. Hemostasis clips are often deployed via endoscopes to stop internal bleeding by holding together edges of wounds or incisions to allow natural healing processes to close the wound. Specialized endoscopic clipping devices are used to deploy the clips at desired locations of the body after which the clip delivery device is withdrawn, leaving the clip within the body.

SUMMARY OF THE INVENTION

The present invention relates to a medical device including a release mechanism, comprising a capsule extending longitudinally from a proximal end to a distal end and including a lumen extending therethrough, the proximal end of the capsule including a plurality of windows extending therethrough and a bushing extending from a proximal end to a distal end and including a channel extending therethrough, the distal end including a plurality of arms extending distally therefrom such that a corresponding one of the arms is releasably engagable with a corresponding one of the windows of the capsule along with a core member including a locking portion and a plurality of engaging elements, the locking portion sized and shaped to be received within the channel of the bushing to apply a radially outward pressure to the arms such that the arms engage the windows of the capsule, the plurality of engaging elements extending laterally outward from a portion of the core member distal of the locking portion such that, each of the engaging elements engage a corresponding one of the arms to deform the arms radially inward and out of engagement with the windows of the capsule.

DETAILED DESCRIPTION

Figure 1:
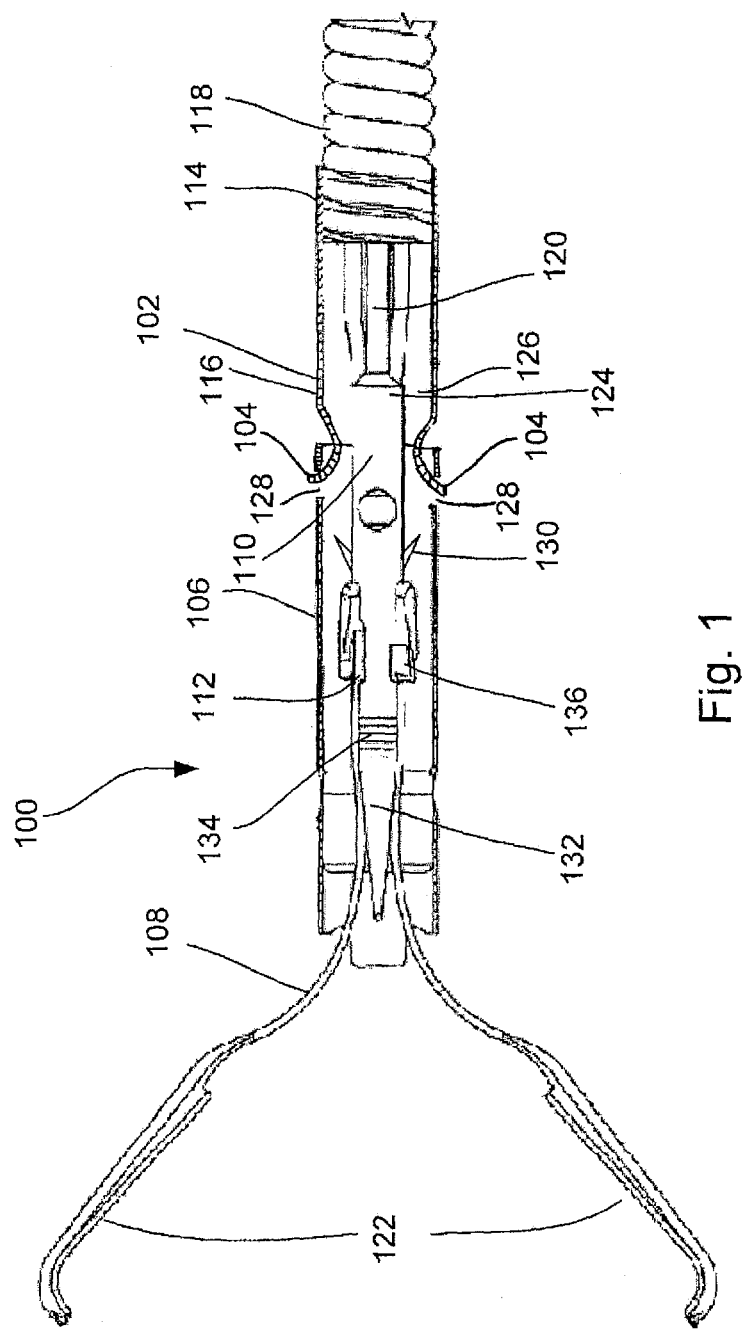
FIG. 1 shows a partially cross-sectional side view of a device according to an exemplary embodiment of the present invention.

The present invention may be further understood with reference to the following description and the appended drawings, wherein like elements are referred to with the same reference numerals. The present invention relates to endoscopic devices as well as elongate medical devices used without an endoscope. In particular, the invention relates to a device in which a distal portion is deployed through a single stage process. Exemplary embodiments of the present invention describe a release mechanism comprising a core member including an engaging element extending therefrom to engage arms of a bushing, through which the core member passes, such that the bushing is released from a capsule of a hemostasis clipping device to deploy a clip as described, for example, in U.S. Publ. Appln. No. 2008/0306491 to Cohen et al. and entitled "Single Stage Hemostasis Clipping Device" and U.S. Publ. Appln. No. 2011/0046651 to Cohen et al. and entitled "Multifunctional Core for Two-Piece Hemostasis Clip," the entire disclosures of which are incorporated herein by reference. Although the exemplary embodiments specifically describe a clipping device, it will be understood by those of skill in the art that the release mechanism of the present invention may be utilized with any device requiring detachment from a catheter or tube at a location remote from an operator within a living body.

Figure 2:
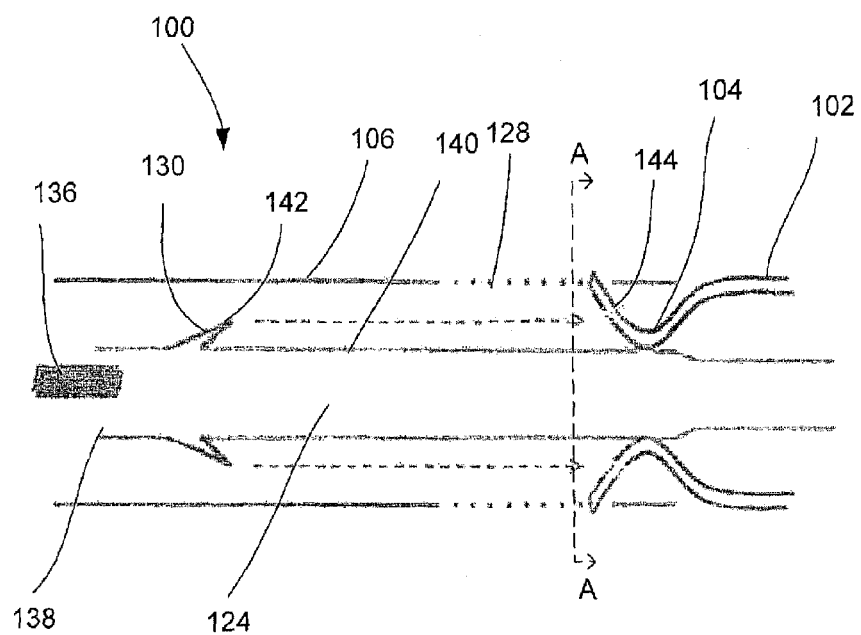
FIG. 2 shows a cross-sectional side view of a release mechanism of the device of FIG. 1.
Figure 3:
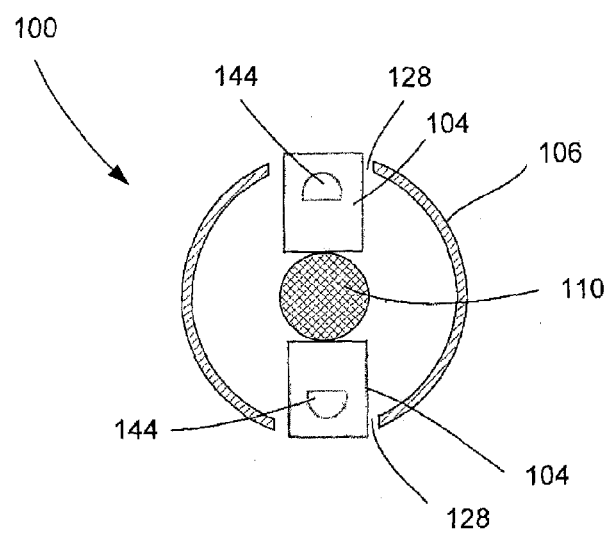
FIG. 3 shows a lateral cross-sectional view of the release mechanism of FIG. 1, along the line A-A.

As shown in FIGS. 1-3, a clipping device 100 according to an exemplary embodiment of the present invention comprises a bushing 102 including a plurality of cantilever arms 104 releasably engaging a capsule 106 which houses a clip 108 therein. The device 100 further comprises a core member 110 coupled to a proximal end 112 of the clip 108. The core member 110 is slidably received within the capsule 106 and the bushing 102 for movement between first and second configurations as will be described in more detail below. In this embodiment, the cantilever arms 104 are substantially hook-shaped to engage the windows 128 in the capsule 106 to releasably couple to the bushing 102 to the capsule 106. The cantilever arms 104 in this embodiment are biased toward a centerline of the bushing 102 so that, when unconstrained, they do not engage the capsule windows 128, de-coupling the capsule 106 from the bushing 102. It will be understood by those of skill in the art, however, that the cantilever arms 104 may be any of a variety of shapes and may be biased toward a position in which they engage the capsule windows 128 so long as, the arms 104 engage the capsule windows 128 before the clip 108 has been deployed. As made clear below, the arms 104 are mechanically deformed and pulled out of engagement from the capsule windows 128 after the clip 108 has been deployed and thus, disengagement does not rely solely on the bias of the arms 104. In the first configuration, a proximal portion 124 of the core member 110 is received within a distal end of a channel 126 of the bushing 102 such that the arms 104 of the bushing 102 are held radially outward in engagement with windows 128 extending through a proximal end of the capsule 106. The core member 110 includes a plurality of engaging elements 130 extending laterally outward from a distal end of the proximal portion 124 such that when the core member 110 is moved proximally relative to the capsule 106 into the second configuration, each of the engaging elements 130 engages a corresponding one of the cantilever arms 104 to deform the arms 104 radially inward, away from the corresponding window 128. It is noted that although the embodiment of FIGS. 1-3 depict two engaging elements 130, any number of engaging elements 130 may be used without deviating from the scope of the invention (e.g., one, three, four, etc.) and to aid in disengagement of the bushing 102 from the capsule 106, as will be described in greater detail with respect to the exemplary method below. Thus, the cantilever arms 104 are released from the capsule 106 separating the capsule 106 and the clip 104 from the bushing and the proximal portion of the device 100.

Specifically, the proximal portion of the device 100 includes the bushing 102 a proximal end 114 of which may be coupled to a flexible insertion member 118 which extends out of the body to an actuation handle accessible to a user of the device 100. A distal end 116 of the bushing 102 is coupled to the capsule 106 via the arms 104 as described above. In one exemplary embodiment, the bushing 102 is substantially cylindrical. It will be understood by those of skill in the art, however, that the bushing 102 and capsule 108 may take any shape desired for a particular application without departing from the scope of the invention. The insertion member 118 is an elongated member extending between a proximal end coupled to an actuating handle (not shown) and a distal end connected to the bushing 102. As those skilled in the art will understand, the insertion member 118 is formed of a material sufficiently flexible to allow it to be advanced through a natural body lumen without damaging the tissue thereof and will have a length suited to the requirements of a procedure being performed. The device 100 further comprises a control element 120 extending through the insertion member 118 between the handle and the clip 108. The control element 120 extends through the insertion member 118 and the bushing 102 from a proximal end coupled to the handle to a distal end connected to the clip 108 via the core member 110 such that movement of an actuating mechanism of the handle moves the clip 108 between an open and a closed configuration via the handle. For example, as the control member 120 is moved distally relative to the capsule 106, clip arms 122 are extended distally from a distal end of the capsule 106. When extended distally from the capsule 106, the clip arms 122 separate from one another (e.g., under a natural bias) into an open configuration to receive a target tissue therebetween. The control member 120 may be moved proximally relative to the capsule 106 to pull the clip 108 back into the capsule 106 so that contact between the capsule 106 and the clip arms 122 draws the clip arms 122 together into the closed configuration gripping target tissue received therebetween.

The core member 110 includes the proximal portion 124 and a distal portion 132 connected to one another via a frangible link 134 designed to fail when subject to a predetermined load. As discussed above, the proximal portion 124 is sized and shaped to be received within the channel 126 of the bushing 102 such that the arms 104 are held radially outward in engagement with the windows 128 of the capsule 106. When the core member 110 is received within the bushing 102, the core member 104 forms a plug which pushes the cantilever arms 104 radially outward maintaining them in a locked position in the windows 128 coupling the bushing 102 to the capsule 106. The core member 110 further includes clip hooks 136 at a distal end 138 of the proximal portion 124 for receiving proximal ends 112 of the clip arms 122. The engaging elements 130 extend laterally outward from the core member 110 proximally of the clip hooks 136. Each of the engaging elements 130 corresponds to a selected one of the arms 104 and is positioned about a perimeter of the core member 110 in alignment with the corresponding cantilever arm 104. The engaging elements 130 may extend radially outward from an outer surface 140 of the core member 110 angled proximally relative to a longitudinal axis of the core member 110 such that a tip 142 of each engaging element 130 is proximal of a point at which the engaging element joins the core member 110. Each of the engaging elements 130 is sized and shaped to engage an opening 144 extending through the corresponding arm 104 so that, as the proximal portion 124 is drawn proximally relative to the capsule 106, the engaging element 130 is received within the corresponding opening 144. Thus, further proximal movement of the proximal portion 124 draws the arms 104 proximally, deforming the arms 104 and drawing them out of engagement with the capsule windows 128. The angled configuration of the engaging elements 130 ensures that, as the engaging element 130 is received proximally within the opening 144, the arms 104 are drawn radially inward out of engagement with the windows 128 as the engaging elements 130 move proximally.

So, when a user is prepared to lock and deploy a clip 108, the control member 120 is drawn proximally to grip target tissue. The user then draws the control member 120 further proximally until the tension applied to the frangible link 134 via the control member 120 exceeds the failure level of the frangible link 134, severing the link 134 and freeing the proximal portion 124 to move proximally through the capsule 106 while the distal portion 132 remains within the capsule 106. Drawing the proximal portion 124 proximally relative to the capsule 106 releases the proximal end 112 of the clip 108 from the clip hooks 136 freeing the clip hooks 136 to spring radially outward into engagement with the windows 128 locking the clip closed over the target tissue. At the same time, the engaging elements 130 are received within the corresponding openings 144 of one of the arms 104 to free the capsule 106 from the bushing 102 as described above.

Figure 4:
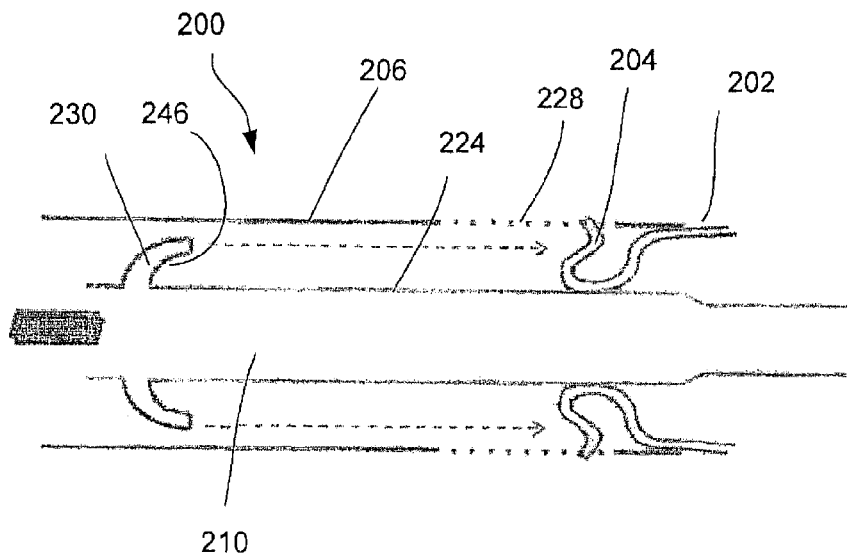
FIG. 4 shows a cross-sectional side view of a release mechanism according to another exemplary embodiment of the present invention.

As shown in FIG. 4, a device 200 is substantially similar to the device 100 described above, comprising a bushing 202 releasably coupled to a capsule 206 via arms 204 of the bushing 202 and a core member 210 slidably received within the capsule 206 and the bushing 202 which moves the arms 204 of the bushing 202 into and out of engagement with capsule windows 228 in a manner similar to that described above. Similarly to the device 100, a proximal portion 224 of the core member 210 is sized and shaped such that, when received within the bushing 202, the arms 204 are moved radially outward into engagement with the capsule windows 228 to couple the capsule 206 and the bushing 202 together. Along a distal end of the proximal portion 224, the core member 210 includes engagement elements 230 extending radially outward therefrom such that, when the proximal portion 224 is drawn proximally relative to the capsule 206, the engagement elements 230 engage the arms 204 deforming the arms 204 and drawing them out of engagement with the capsule windows 228. The engagement elements 230 of this embodiment are sized and shaped to interlock with correspondingly sized and shaped arms 204. For example, proximal-facing surfaces of the engagement elements 230 according to this embodiment are curved to form concave surfaces 246 which face the cantilever arms 204. The arms 204 according to this embodiment are correspondingly convexly shaped such that when received within the concave surfaces 246, the arms 204 and the engaging elements 230 are interlocked ensuring that the arms 204 are deformed radially inward and out of engagement with the capsule windows 228 as the proximal portion 224 is moved proximally past the proximal end of the capsule 206. Although the exemplary embodiment specifically describes and shows correspondingly curved engagement elements 230 and arms 204, it will be understood by those of skill in the art that the engagement elements 230 and the arms 204 may have any of a variety of corresponding shapes so long as the engagement elements 230 interlock with the arms 204 to deform the arms 204 and draw the arms 204 out of engagement with the capsule windows 228.

Figure 5:
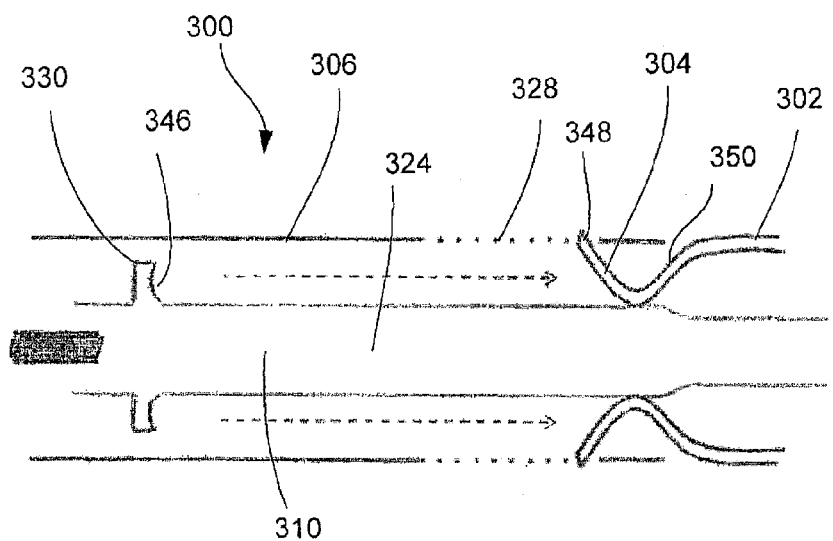
FIG. 5 shows a cross-sectional side view of a release mechanism according to yet another exemplary embodiment of the present invention.

As shown in FIG. 5, a device 300 according to another exemplary embodiment of the present invention is substantially similar to the devices 100, 200 described above, comprising a bushing 302 releasably coupled to a capsule 306 via arms 304 received in windows 328 of the capsule 306 and a core member 310 slidably received within the bushing 302 and the capsule 306 for moving the aims 304 of the bushing 302 into and out of engagement with capsule windows 328. Similarly to the core member 210, the core member 310 includes a proximal portion 324 which, when received within the bushing 302, moves cantilever arms 304 radially outward to engage the capsule windows 328. Along a distal end of the proximal portion, the core member 310 includes engagement elements 330 for engaging the cantilever arms 304 to deform the arms 304 radially inward and out of engagement with the capsule windows 328 as the proximal portion 324 is drawn proximally relative to the capsule 306. The engagement elements 330 also include a curved surface 346 facing the bushing 302. However, the curved surface 346 is not sized and shaped to interlock with the cantilever arms 304 in the same manner as in the device 200. Rather, the curved surface 346 here is treated with a material having adhesive qualities such that when the surface 346 of the engaging element 330 comes into contact with the arms 304, the arms 304 adhere to the engagement element 330 from a distal end 348 of the arms 304 toward a proximal end 350 thereof such that the arms 304 are drawn radially inward out of engagement with the capsule windows 328. As would be understood by those skilled in the art, the material with which the curved surface 346 may be treated may be any suitable biocompatible adhesive material. Alternatively, the material may be a polymer which mimics adhesive behavior. In an exemplary embodiment, the material may be a biocompatible pressure sensitive adhesive (PSA) having elastomeric properties. Specifically, the engagement elements 330 may be coated with the PSA while the bushing arms arm are coated with a corresponding adherent, as those skilled in the art will understand. The adherent coating on the arms 304 may be configured to exhibit the required adhesive properties at room temperature. In another embodiment, the material may be a polymer configured to mimic adhesion instead of being inherently adhesive. Specifically, the arms 304 may be coating with a gummy/flexible substrate (e.g., an elastomer with mechanical properties similar to those of biological tissue) and the engagement elements 330 may be coated with a micropatterned layer of polymer material (e.g., flowable silicones including but not limited to silicones that have been thinned to be rendered flowable, etc.). The micropatterned layer on the engagement element 330 (not shown) creates a mechanical interlock with the substrate on the bushing arm 304 to aid in retraction of the arms 304 radially inward and out of engagement with the windows 328. In some embodiments, the engaging elements 330 can be secured onto, over or around the arms 304 of the bushing 302 to assist in the removal of the arms 304 from the capsule windows 328.

In another embodiment of the invention, the arms 104, 204, 304 may be biased to fold or collapse once a force from the engaging elements 130, 230, 330 reaches a predetermined level. Specifically, a shape of the arms 104, 204, 304 may be biased to include a fold line permitting folding thereof.

It will be apparent to those skilled in the art that various modifications and variations can be made in the structure and the methodology of the present invention, without departing from the spirit or scope of the invention. For example, the bushing 102, 202, 302 may include any number of arms 104, 204, 304 extending therefrom. In another example, a material thickness and/or width of the arms 104, 204, 304 may be altered to be more flexible or softer in certain portions. Thus, it is intended that the present invention cover the modifications and variations of this invention provided that they come within the scope of the appended claims and their equivalents.

What is claimed is:

1. A tissue clipping device, comprising:
a distal portion sized and shaped for insertion into a body lumen, the distal portion including a clip having a first clip arm, a proximal end of the clip movably housed within a lumen of a capsule extending longitudinally from a proximal end to a distal end such that the clip is movable relative to the capsule between a tissue receiving configuration in which the first clip arm extends distally from a distal end of the capsule in a biased open position and a tissue gripping configuration in which the first arm is retracted proximally within the capsule, the capsule including a first window extending laterally through a proximal end thereof;
a bushing extending from a proximal end to a distal end and including a channel extending therethrough, the distal end including a first bushing arm extending distally therefrom such that the first bushing arm is releasably engagable with the first window of the capsule; and
a core member received within the capsule and coupled to a proximal end of the clip arms, the core member including a locking portion and a first engaging element, the locking portion sized and shaped to be received within the channel of the bushing to apply a radially outward pressure to the first bushing arm such that the first bushing arm engages the first window of the capsule, the first engaging element extending radially outward from a portion of the core member distal of the locking portion such that the first engaging elements engages the first bushing arm to deform the first bushing arm radially inward and out of engagement with the first window of the capsule.

2. The device of claim 1, further comprising a second window on the capsule and a second bushing arm formed on the distal end of the bushing, the first and second bushing arms being positioned such that a corresponding one of the first and second bushing arms releasably engages a corresponding one of the first and second windows.

3. The device of claim 2, further comprising a second engaging element formed on the core member, the second engaging element extending radially out of the core member distal of the locking portion such that each of the first and second engaging elements engages and deforms a corresponding one of the first and second bushing arms radially inward and out of engagement with the first and second windows of the capsule, respectively.

4. The device of claim 3, wherein the first and second engagement elements are angled with respect to a longitudinal axis of the core member such that a tip thereof is pointed toward a proximal end of the device, the engaging elements being sized and shaped to be received within corresponding holes extending through each of the first and second bushing arms.

5. The device of claim 3, wherein the first and second engagement elements and the first and second bushing arms are correspondingly sized and shaped such that the first and second engagement elements and the first and second arms interlock with one another.

6. The device of claim 3, wherein the first and second engagement elements comprise respective concave proximal surfaces which are shaped to interlock with the first and second arms, respectively.

7. The device of claim 1, wherein the first engagement element is treated with a material having adhesive properties to adhere to the first arm.

8. The device of claim 7, wherein the material is one of an adhesive and a polymer.

9. The device of claim 1, wherein the core member includes a proximal portion and a distal portion connected to one another via a frangible link configured to fail when subject to a predetermined load, the locking portion and the first engagement element extending along the proximal portion so that, when the frangible link is severed, the distal portion remains within the capsule while the proximal portion is moved proximally relative to the capsule.

* * * * *